United States Patent [19]

Ounanian et al.

[11] Patent Number: 4,988,502
[45] Date of Patent: Jan. 29, 1991

[54] MASCARA COMPOSITION

[75] Inventors: Hovig O. Ounanian, Princeton Junction; Kenneth A. Cohen, Aberdeen; Joseph DiSomma, Ramsey; Harvey Gedeon, Allendale, all of N.J.

[73] Assignee: Revlon, Inc., New York, N.Y.

[21] Appl. No.: 408,539

[22] Filed: Sep. 18, 1989

[51] Int. Cl.$^5$ .................. A61K 7/02; A61K 7/032
[52] U.S. Cl. ............................ 424/63; 424/64; 424/70
[58] Field of Search ..................... 424/63, 64, 70

[56] References Cited

U.S. PATENT DOCUMENTS

| | | | |
|---|---|---|---|
| 3,911,105 | 10/1975 | Papantoniou et al. | 424/64 |
| 3,937,811 | 2/1976 | Papantoniou et al. | 424/64 |
| 4,490,179 | 12/1984 | Bernhard | 106/419 |
| 4,536,405 | 8/1985 | Nara et al. | 514/781 |
| 4,537,782 | 8/1985 | Millet et al. | 514/774 |
| 4,622,074 | 11/1986 | Miyoshi et al. | 106/419 |
| 4,828,826 | 5/1989 | Franz | 424/63 |
| 4,839,163 | 6/1989 | Busch, Jr. | 424/63 |
| 4,877,604 | 10/1989 | Schlossman | 424/64 |

*Primary Examiner*—Merrell C. Cashion, Jr.
*Assistant Examiner*—Amy L. Hulina

[57] ABSTRACT

A mascara composition is disclosed. The composition comprises a cosmetically acceptable hydrophobic pigment, a film-forming resin, a water dispersible thickening agent, a humectant and water. The treatment to make the pigment hydrophobic is preferably accomplished by treating the pigment or pigments with lecithin.

10 Claims, No Drawings

MASCARA COMPOSITION

BACKGROUND OF THE DISCLOSURE

1. Field of the Invention

Mascara is a major cosmetic product, of significant importance to the cosmetic industry. Mascara is utilized to enhance female beauty by coating eyelashes and, in some cases, eyebrows to make them more attractive by providing color thereto. Although this product has obviously attained commercial acceptance, mascara compositions have been criticized by many users. The complaints raised against the use of mascara range from heavy feel, heavy coating and smudging of eyelashes to difficulty of removal from the delicate eye area, potential for loss and even loss of eyelash hairs.

Those skilled in the art are aware that the basis for these criticisms lie in the inclusion of high concentration of color pigments, waxes, heavy oils, plasticizers, heavy film-formers and the like in mascara compositions. These ingredients are essential in prior art mascara compositions in that they disperse the pigments which are included therein to provide color.

The inclusion, in prior art mascara compositions, of significant concentration of pigment is in part caused by the aforementioned inclusion of waxes, heavy oils, plasticizers and heavy film formers. These ingredients have a tendency to render the mascara composition pale or light in color. That is, the heavy concentration of waxes, oils and the like make necessary the loading of high concentrations of pigment to provide the necessary color. This heavy loading of pigment sometimes results in smudging of the composition.

To overcome this recognized problem in the art, producers have recently introduced so-called "no-color" mascara compositions. These compositions overcome the problems associated with waxes, heavy oils, heavy film formers, plasticizers and the like by the simple expedient of not including them in the composition. They are able to accomplish this in that they do not include pigments in the mascara. The absence of pigments, of course, permits the non-inclusion of waxes, heavy oils, heavy film formers, plasticizers and the like in that these components are employed in prior art mascara compositions.

Although this advance in the art overcomes the problems associated with the presence of high concentrations of waxes, oils and the like, this product has also been criticized by users. That criticism resides in the fact that the absence of pigment reduces the attractiveness of utilizing a mascara for those users who have light colored lashes. In these cases, the absence of color in these mascaras reduces the beauty enhancement provided by the product.

Obviously, there exists a need in the art to develop a mascara composition which does not include waxes, heavy oils, heavy film formers, plasticizers and the like without forfeiting the attractive features of prior art mascara compositions, that is, providing bright color highlights to the eyelashes.

2. Background of the Prior Art

The prior art includes a plurality of mascara composition products which are advertised as "clear mascaras." These mascara compositions are characterized by the absence of heavy oils, waxes and other ingredients which have a heavy and sticky effect on the eyelashes. However, while these products are lightweight and non-sticky, they do not provide color to the eyelashes upon which they are applied. The reason for this is that almost all of them do not include sufficient pigment concentration to impart color to eyelashes. At most, such products are colored to the extent that they color the composition in the container in which the mascara composition is sold. That is, the concentration of pigment in this mascara composition is so small that it is subject to the same objections lodged against pigment-free mascara compositions, i.e., the absence of color reduces its beauty enhancement effect compared to the traditional mascara compositions of the prior art.

The mascara compositions described in the prior art do not include any teachings directed to the use of a hydrophobic coated pigment. There are, however, disclosures in the prior art directed to a formation of hydrophobic pigments useful in other cosmetic applications. One such teaching is U.S. Pat. No. 4,490,179 to Bernhard which sets forth a process for rendering nacreous pigments hydrophobic by coating these pigments with an aqueous suspension of a chromium (III) or aluminum (III) hydroxide or silicate followed by treatment of the coated pigment with a solution of a hydrocarbon carboxylic acid having more than four carbon atoms per carboxyl group. Nacreous pigments are pigments formed from mica platelets coated with metal oxides. These pigments are commonly employed in such cosmetic compositions as nail lacquers, lipsticks and powders.

U.S. Pat. No. 4,622,074 to Miyoshi et al. describes the coating of pigments or extender pigment surfaces with hydrogenated lecithin or the reaction product of hydrogenated lecithin and a water-soluble metal salt. These coated pigments are utilized in make-up cosmetics such as powder foundation, rouge and eyeshadow compositions. The lecithin coating of the pigments used in these make-up cosmetics are said to improve many of the properties of these products Cosmetic compositions which include lecithin coated pigments are said to be more water repellant. Furthermore, they spread easily in that they are smooth, having a moisturizing effect on the skin.

Although the two above-recited references describe the use of hydrophobic pigments in cosmetic applications, neither of them suggest the use of a hydrophobic pigment in a mascara composition nor do they teach a mascara composition having the desirable properties noted above.

BRIEF SUMMARY OF THE INVENTION

A new cosmetic composition useful as a mascara has now been developed which provides the brilliant color highlights necessary for mascara effectiveness but which eliminates the need for waxes, heavy oils, heavy filmformers, plasticizers and the like. These ingredients have long been associated with problems ascribed to the mascara compositions of the prior art. Thus, the new mascara composition eliminates the heaviness, waxiness and unhealthy effects on eyelashes caused by the use of the mascara compositions of the prior art.

In accordance with the present invention, a mascara composition is provided. This composition comprises at least one cosmetically acceptable hydrophobic pigment, a film-forming resin, a water dispersible thickening agent, a humectant and water.

DETAILED DESCRIPTION

The mascara composition of the present application incorporates therein at least one cosmetically acceptable hydrophobic colorant. Preferably, an agent is utilized to convert a water dispersible colorant to a non-water dispersible colorant. Specifically, a hydrophobic agent is coated onto at least one cosmetically acceptable colorant. Hydrophobic agents useful in providing this function include lecithin, dimethicone, dimethicone and mineral oil, polyethylene, isopropyl triisostearyl titanate, calcium stearate, isostearic acid and the combination of squalane, beeswax and lauric acid. All of these specific hydrophobic agents are reported in the CTFA Cosmetic Ingredient Dictionary, Third Edition or Third Edition, Supplement, published by the Cosmetic, Toiletry and Fragrance Association, Inc., Washington, D.C.. These dictionary volumes, published 1982 and 1985, respectively, are incorporated herein by reference. Of the acceptable hydrophobic agents lecithin is preferred.

Among the colorants hydrophobically treated in accordance with this invention are such cosmetically acceptable colorants as carmine, bismuth oxychloride, iron oxides, zinc oxide, kaolin, ultramarine blue, ultramarine green, ultramarine pink, ultramarine red, ultramarine violet, chromium hydroxide green, chromium oxide greens, silica and manganese violet. Of these pigments, within the contemplation of the composition of the present invention, chromium hydroxide green, ultramarine blue and the iron oxides: iron oxide black, iron oxide yellow and iron oxide red are particularly preferred. All of the aforementioned pigments are fully defined in the CTFA Cosmetic Ingredient Dictionary, Third Edition or Third Edition Supplement incorporated herein by reference.

In a preferred embodiment, a cosmetically acceptable pigment treated with a hydrophobic agent, hereinafter referred to as the hydrophobic pigment, comprises between about 1% and about 12% by weight, based on the total weight of the mascara composition. More preferably, the hydrophobic pigment comprises between about 2% and about 10% by weight, based on the total weight of the mascara composition. Still more preferably, the hydrophobic pigment is present in a concentration in the range of between about 2% and about 8% by weight, based on the total weight of the mascara composition. Even still more preferably, the hydrophobic pigment constitutes between about 2% and about 5% by weight, based on the total weight of the mascara composition.

A second critical ingredient in the mascara composition of this invention is a film forming resin. Film forming resins within the contemplation of the present invention include polyvinyl alcohol, polyvinyl acetate, PVP, ammonium acrylates copolymer, cellulose gum, carboxymethyl hydroxyethylcellulose, acrylate/ammonium methacrylate copolymer and acrylic/acrylate copolymer. These resins are fully defined in the CTFA Cosmetic Ingredient Dictionary, Third Edition and Third Edition, Supplement which are again incorporated herein by reference.

Those skilled in the art appreciate that the film forming polymers used in the mascara composition of the present invention do not produce sticky type products characteristic of the mascara compositions of the prior art. Of these preferred film forming polymers, polyvinyl alcohol is particularly preferred for use in the mascara composition of this invention.

The film forming resin constituent of the cosmetic composition of the present invention represents about 0.5% to about 4% by weight. Preferably, the film forming resin is present in the composition in a concentration in the range of between about 0.8% and about 2.5% by weight. Most preferably, the film forming resin is present in the composition in a concentration in the range of between about 0.9% and about 1.5%, all said percentages being by weight, based on the total weight of the mascara composition.

A third essential component of the mascara composition is a water dispersible thickening agent. A particularly preferred water dispersible thickening agent, within the contemplation of the mascara composition of this invention, is the combination of a base and a polymeric acid. Among the bases that may be employed to form the water dispersible thickening agent is triethanolamine, isopropanolamine, diisopropanolamine, ethanolamine, sodium hydroxide and potassium hydroxide. Of the polymeric acids within the contemplation of the water dispersible thickening agent are polymers of acrylic acid cross linked with polyfunctional agents such as Carbomer 910, Carbomer 934, Carbomer 934P, Carbomer 940 and Carbomer 941.

The base and the polymeric acid are separately introduced into the composition. However, the two components react on contact to form the water dispersible thickening agent. Of the above-recited bases and polymeric acids, triethanolamine (TEA) and Carbomer 940, respectively, are particularly preferred. Thus, the water thickening agent "TEA-Carbomer 940" is most preferred.

The CTFA Cosmetic Ingredient Dictionary, Third Edition and Third Edition, Supplement recite a plurality of cosmetically acceptable components denoted as combinations of triethanolamine and other cosmetically acceptable components. These combinations of ingredients, the triethanolamine salt of the other component, are typically denoted as TEA-followed by the name of the second ingredient. The Cosmetic Ingredient Dictionary, Third Ed. or Third Ed., Supplement does not include "TEA-Carbomer 940." Suffice it to say, this combination is formed immediately upon the combining of triethanolamine and Carbomer 940, components defined in said Dictionary. The two components rapidly react to form a complex.

In addition to TEA-Carbomer 940 other preferred species which may be used as the water dispersible thickening agent of the mascara composition include magnesium aluminum silicate, TEA-Carbomer 910, TEA-Carbomer 934, TEA-Carbomer 934P, TEA-Carbomer 941, isopropylamine-Carbomer 940, sodium hydroxide-Carbomer 940, potassium hydroxide-Carbomer 940, cellulose gum and xanthan gum. All of these components are fully defined and described in the aforementioned CTFA Cosmetic Ingredient Dictionary, Third Edition and Third Edition, Supplement incorporated herein by reference. As in the case of TEA-Carbomer 940, the other base-Carbomer combinations are formed in-situ upon contact between the base and the Carbomer polymer.

The water dispersible thickening agent represents between about 0.5% and about 5% of the mascara composition. Preferably, the water dispersible thickening agent is present in a concentration in the range of between about 1% and about 4% of the mascara composition. More preferably, the water dispersible thickening agent represents between about 2% and about 3.5% of the mascara composition. All of the above recited percentages are by weight, based on the total weight of the mascara composition.

A fourth essential ingredient of the composition of this invention is a humectant. Humectants within the contemplation of the cosmetic composition of the present invention include glycerin, sorbitol, propylene glycol, glycol, glycol dibehenate, glycol dioctanoate, glycol distearate, glycol hydroxystearate, glycol oleate, glycol ricinoleate, glycol salicylate, glycol stearate, glycol stearate SE, sodium PCA and mixtures thereof. Of these humectants, glycerin is particularly preferred.

The humectant component of the mascara composition is representative of between about 0.1% and about 3% of the composition. Preferably, the humectant comprises between about 0.2% and about 2% of the mascara composition. More preferably, the concentration of humectant is between about 0.3% and about 1% of the mascara composition. These percentages are by weight, based on the total weight of the mascara composition.

In addition to the above essential ingredients of the mascara composition other components may be included in preferred embodiments of the composition. These optional components include a moisturizing agent. Moisturizing agents useful in the mascara composition of this invention include hydrolyzed elastin, hydrolyzed keratin, hydrolyzed silk, hydrolyzed animal protein, hydrolyzed milk protein, hydrolyzed mucopolysaccharides, potassium coco-hydrolyzed animal protein, myristoyl hydrolyzed animal protein and mixtures thereof as defined in the CTFA Cosmetic Ingredient Dictionary, Third Edition. In a preferred embodiment, the moisturizing agent is present in a concentration in the range of between about 0.01% and about 1% by weight, based on the total weight of the mascara composition.

Another optional component of the mascara composition preferred for use in this invention is one or more preservatives. Preservatives especially useful in the mascara composition are imidazolidinyl urea, diazolidinyl urea, Quaternium-15, methylparaben, ethylparaben, propylparaben, butylparaben, EDTA and mixtures thereof. These preservatives are defined in detail in the CTFA Cosmetic Ingredient Dictionary, Third Edition which is incorporated herein by reference. Of these preservatives, imidazolidinyl urea, methylparaben and mixtures thereof are particularly preferred for use in the mascara composition. The preferred concentration of preservatives used in the mascara composition is in the range of between about 0.01% and about 0.5% by weight, based on the total weight of the mascara composition.

Still another optionally included component in the mascara composition of this invention is a sequestering agent. A sequestering agent is preferably present in a concentration in the range of between about 0.01% and about 0.1% by weight, based on the total weight of the mascara composition Preferred sequestering agents for use in this composition include disodium EDTA and trisodium EDTA. These agents are completely identified in the aforementioned CTFA Cosmetic Ingredient Dictionary, Third Edition. Of these, trisodium EDTA is particularly preferred for use in the mascara composition.

A final optional component that is preferably included in the mascara composition is a drying agent. Drying agents are preferably present in the mascara composition in a concentration in the range of between about 1% and less than 5% by weight, based on the total weight of the composition. The preferred drying agents for use in this composition are isopropyl alcohol one or more of the SD alcohols. A plurality of SD alcohols are defined in the CTFA Cosmetic Ingredient Dictionary, Third Edition. Specifically, any of the SD alcohols, SD Alcohol 1 to SD Alcohol 46, listed in the CTFA Cosmetic Ingredient Dictionary, Third Edition, incorporated herein by reference, may be used in the mascara composition of this invention. A particularly preferred drying agent is SD Alcohol 40-B.

The remainder of the mascara composition comprises water. Water, an essential ingredient, is present in a concentration in the range of between about 60% and about 95%, preferably, between about 75% and about 90%, most preferably, between about 85% and about 90%. All of these percentages are by weight based on the total weight of the mascara composition.

Preferred embodiments of the present mascara composition focus on compositions which provide brilliant colors, albeit utilizing pigments in concentrations significantly lower than those utilized in the mascara compositions of the prior art. In these preferred embodiments, the mascara composition commonly comprises about 0.9% to about 1.1% polyvinyl alcohol; about 0.4% to about 0.6% glycerin; about 0.03% to about 0.07% trisodium EDTA; about 0.005% to about 0.02% imidazolidinyl urea; about 0.0125% to about 0.50% methylparaben; about 0.03% to about 0.07% hydrolyzed animal protein; about 4% to less than 5% SD Alcohol 40-B. All of the above recited percentages are by weight, based on the total weight of the mascara composition.

All of the preferred mascara compositions of this invention additionally include the water dispersible thickening agent, TEA-Carbomer 940. However, the concentration of this component, which as stated above is the reaction product of triethanolamine and Carbomer 940, varies between about 2.85% and about 3.375% depending upon the desired mascara color. In a preferred embodiment wherein a green color is desired, the concentration of TEA-Carbomer 940 is in the range of between about 2.85% and about 3.05%. In a preferred embodiment wherein a brown colored mascara is produced, the TEA-Carbomer 940 component comprises between about 3.20% and about 3.34%. The same concentration range of TEA-Carbomer 940, between about 3.20% and about 3.34%, is used in the preferred embodiment wherein a blue mascara is produced Finally, in an embodiment to produce a black colored mascara composition the concentration of TEA-Carbomer 940 is in the range of between about 3.175% and about 3.375%. Again, all of these percentages represent concentration by weight, based on the total weight of the mascara composition.

Another component of preferred compositions to produce green, brown, blue and black colored mascaras is between about 1.7% and about 4.2% of a lecithin-treated cosmetically acceptable pigment. In the embodiment wherein a green colored mascara composition is produced, the composition includes between about 3.8% and about 4.2% of chromium hydroxide green. In the preferred embodiment resulting in the formation of a brown colored mascara composition, the composition includes between about 0.5% to about 0.7% lecithin-treated iron oxide black; between about 0.6% to about 0.8% lecithin-treated iron oxide yellow; and between about 0.6% to about 0.8% lecithin treated iron oxide red. The preferred blue colored mascara is produced using a mascara composition that includes between about 2.8% to about 3.2% of lecithin-treated ultramarine blue. Finally, in the preferred embodiment wherein a black colored mascara composition is provided, the composition incorporates between about 2.3% and about 2.7% of lecithin-treated iron oxide black. The usual caveat that percentages are by weight, based on the total weight of the mascara composition, applies to the recitation of lecithin-treated pigment concentrations.

The final component of the preferred compositions, to produce green, brown, blue and black colored mascara compositions, is water. Water is present in a concentration of between about 85% and about 90% by weight. However, specific mascara compositions have narrower concentrations within this range. For example, in the embodiment wherein a green mascara composition is formed, water is present in a concentration of between about 85% and about 88%. Water represents between about 87% and about 90% of the brown colored mascara composition. The blue colored mascara composition comprises between about 86% and about 89% water. The water component of the black colored mascara composition is between about 85% and about 88%. All said percentages are again by weight, based on the total weight of the mascara composition.

The following examples are given to illustrate the scope of the present invention. Because these examples are given for illustrative purposes only, the invention should not be inferred to be limited to these examples.

EXAMPLE 1

Preparation of a Black Colored Mascara Composition

A black colored mascara composition was prepared by charging about 16.9 parts (by weight) water into a steam jacketed first kettle provided with an agitator. Under agitation 1 part polyvinyl alcohol was added to the water in the first kettle. After mixing for about 15 minutes an additional charge of water equal to that initially charged, about 16.9 parts, was added to the agitated mass in the first kettle. After the second charge of water was added the contents of the first kettle was heated to about 135° F. for about 1 hour under agitation. With no visible solids present 0.05 part of trisodium EDTA and 0.5 part glycerin were added to the contents of the first kettle. The newly added components were added under agitation which was continued for about 15 minutes.

After the contents of the first kettle were visibly completely free of solids, they were transferred to a second steam jacketed, agitator-equipped kettle. The contents during transfer were filtered through a fine mesh filter to insure the absence of solids.

In a separate high shear mixer, equipped with a variable speed propeller, were charged 8 parts water and 1 part of a 2.5% solution of Carbomer 940 in water. These components were agitated while 2.5 parts lecithin treated iron oxide black was added thereto. Agitation was continued until the pigment was completely dispersed. When dispersed, the contents of the high shear mixer were transferred into the second kettle.

A 2.5% solution of Carbomer 940 in water (43 parts) was introduced into a tank provided with an agitator which was activated during introduction of the 2.5% solution. When the ingredients were smooth and lump-free they were transferred from the tank to the second kettle. The contents of the tank were strained through a fine mesh prior to entering the second kettle. The combined contents of the second kettle were agitated for about 30 minutes at a temperature of about 135° F. to make the contents smooth and uniform. The contents of the kettle were then cooled to about 90° F. under agitation.

In a premix container equipped with a propeller 1 part water, 0.05 part hydrolyzed animal protein and 0.01 part imidazolidinyl urea were mixed. These ingredients were dissolved into a liquid mass under agitation provided by the propeller and then transferred into the second kettle which was stirred after that addition for about 10 to 15 minutes.

In another premix container 4.5 parts of SD Alcohol 40-B and 0.2 part methylparaben were introduced and mixed to form a clear solution. This solution was added to the contents of the second kettle and mixing of the newly added contents continued for about 30 minutes.

In still another premix container 2.2 parts triethanolamine and 2.2 parts water were mixed until they were clear and uniform. When clear and uniform this mixture was added to the agitated contents of the second kettle. The contents of the second kettle, the black colored mascara composition, were removed to a storage container.

The composition in the storage container had the constituency summarized in the Table.

EXAMPLE 2

Preparation of a Brown Colored Mascara Composition

A brown colored mascara composition was prepared in accordance with the procedure of Example 1. The only distinctions between the preparation of the composition of Example 1 and the present composition was the identity and amount of the lecithin-treated hydrophobic pigment and the concentrations of the TEA-Carbomer 940 and water components. These differences are set forth in the constituency of the brown colored mascara composition, also included in the Table.

EXAMPLE 3

Preparation of a Blue Colored Mascara Composition

A blue colored mascara composition was prepared in accordance with the procedure of Example 1. The composition, which differed from that of Example 1 in the identity and concentration of the lecithin-treated pigments and the concentration of the TEA-Carbomer 940 and water components, is summarized in the Table.

EXAMPLE 4

Preparation of a Green Colored Mascara Composition

A green colored mascara composition was prepared in accordance with the procedure of Example 1. The composition differed from that of Example 1 only in the concentration of the TEA-Carbomer 940 and water components and the identity and concentration of the lecithin-treated hydrophobic pigments The composition of the green colored mascara composition of this example is summarized in the Table.

TABLE

| Component | Ex. 1 Black Mascara | Ex. 2 Brown Mascara | Ex. 3 Blue Mascara | Ex. 4 Green Mascara |
|---|---|---|---|---|
| Water | 87.865 | 88.34 | 87.34 | 86.70 |
| SD Alcohol 40-B | 4.50 | 4.50 | 4.50 | 4.50 |
| TEA-Carbomer 940 | 3.275 | 3.30 | 3.30 | 2.94 |
| Polyvinyl Alcohol | 1.00 | 1.00 | 1.00 | 1.00 |
| Glycerin | 0.50 | 0.50 | 0.50 | 0.50 |
| Methylparaben | 0.25 | 0.25 | 0.25 | 0.25 |
| Imidazolidinyl Urea | 0.01 | 0.01 | 0.01 | 0.01 |
| Trisodium EDTA | 0.05 | 0.05 | 0.05 | 0.05 |
| Hydrolyzed Animal Protein | 0.05 | 0.05 | 0.05 | 0.05 |
| Lecithin-treated Pigments | | | | |
| Chromiun Hydroxide Green | | | | 4.00 |
| Iron Oxide Black | 2.50 | 0.60 | | |
| Iron Oxide Yellow | | 0.70 | | |
| Iron Oxide Red | | 0.70 | | |
| Ultramarine Blue | | | 3.00 | |

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A mascara composition consisting essentially of between about 1% and about 12% of a cosmetically acceptable pigment treated with lecithin and selected from the group consisting of carmine, bismuth oxychloride, iron oxide black, iron oxide yellow, iron oxide red, zinc oxide, kaolin, ultramarine blue, ultramarine green, ultramarine pink, ultramarine red, ultramarine violet, chromium hydroxide green, chromium oxide greens, silica, manganese violet, and mixtures thereof; between about 0.5 and about 4% of a film-forming resin selected from the group consisting of polyvinyl alcohol, polyvinyl acetate, PVP, ammonium acrylates copolymer, cellulose gum, carboxymethyl hydroxyethylcellulose, acrylate/ammonium methacrylate copolymer and acrylic/acrylate copolymer; between about 0.5% and about 5% of a water dispersable thickening agent which is a complex of triethanolamine and a polymer of acrylic acid cross-linked with a polyfunctional agent, a complex of isopropylamine, sodium hydroxide or potassium hydroxide and a polymer of acrylic acid cross linked with a polyfunctional agent magnesium aluminum silicate, cellulose gum and xanthan gum; and between about 0.1% and about 3% of a humectant selected from the group consisting of glycerin, sorbitol, propylene glycol, glycol, glycol dibehenate, glycol dioctanoate, glycol distearate, glycol hydroxystearate, glycol oleate, glycol ricinoleate, glycol salicylate, glycol stearate, glycol stearate SE, sodium PCA and mixtures thereof; and between about 60 and about 95% of water, all of said percentages being by weight based upon the total weight of the composition.

2. A composition in accordance with claim 1 wherein said lecithin treated pigment is present in a concentration of between about 2% and about 10%; said film forming resin is present in a concentration of between about 0.8% and about 2.5%; said water dispersible thickening agent is present in a concentration of between about 1% and about 4%; said humectant is present in a concentration of between about 0.2% and about 2%; and said water is present in a concentration of between about 75% and about 90%, all said percentages being by weight based on the total weight of said composition.

3. A composition in accordance with claim 2 wherein said lecithin treated pigment is present in a concentration of between about 2% and about 8%; said film forming resin is present in a concentration of between about 0.9% and about 1.5%; said water dispersible thickening agent is present in a concentration of between about 2% and about 3.5%; said humectant is present in a concentration of between about 0.3% and about 1%; and said water is present in a concentration of between about 85% and about 90%, all said percentages being by weight based on the total weight of said composition.

4. A composition in accordance with claim 3 wherein said lecithen treated pigment is present in a concentration of between about 2% and about 5% by weight, based on the total weight of said composition.

5. A composition in accordance with claim 1 additionally containing between about 0.01% and about 1% of a moisturizing agent selected from the group consisting of hydrolyzed elastin, hydrolyzed keratin, hydrolyzed silk, hydrolyzed animal protein, hydrolyed milk protein, hydrolyzed mucopolysaccharides, potassium coco-hydrolyzed animal protein, myristoyl hydrolyzed animal protein and mixtures thereof; between about 0.01% and about 0.5% of a preservative selected from the group consisting of imidazolidinyl urea, diazolidinyl urea, Quaternium-15, methyl paraben, ethyl paraben, propylparaben, butylparaben, and mixtures thereof; between about 0.01% and about 0.1% of a sequestering agent selected from the group consisting of trisodium EDTA and disodium EDTA; and between about 1% and less than 5% of a drying agent selected from the group consisting of isopropyl alcohol or at least one SD alcohol, all said percentages being by weight, based on the total weight of said composition.

6. A mascara composition which comprises between about 2.85% and about 3.375% of a complex of triethanolamine and a polymer of acrylic acid cross-linked with a polyfunctional agent; between about 1.7% and about 4.2% of a lecithin-treated cosmetically acceptable pigment; between about 85% and about 90% water; between about 0.9% and about 1.1% polyvinyl alcohol; between about 0.4% and about 0.6% glycerin; between about 0.03% and about 0.07% trisodium EDTA; between about 0.005% and about 0.125% and about 0.5% methylparaben; between about 0.03% and about 0.07% hydrolyzed animal protein; and between about 4% and about 5% SD Alcohol 40-B, all said percentages being by weight, based on the total weight of said composition.

7. A composition in accordance with claim 6 wherein said complex of triethanolamine and a polymer of acrylic acid cross-linked with a polyfunctional agent is present in a concentration of between about 2.85% and about 3.05%, said lecithin-treated pigment is chromium hydroxide green, present in a concentration of between about 3.8 and about 4.2%; and said water is present in a concentration of between about 85% and about 88%.

8. A composition in accordance with claim 6 wherein said complex of triethanolamine and a polymer of acrylic acid cross-linked with a polyfunctional agent is present in a concentration of between about 3.20% and about 3.40%; said lecithin-treated pigment comprises between about 0.5% and about 0.7% iron oxide black, between about 0.6% and about 0.8% iron oxide yellow and between about 0.6% and about 0.8% iron oxide red; and said water is present in a concentration of between about 87% and about 90%.

9. A composition in accordance with claim 6 wherein said complex of triethanolamine and a polymer of acrylic acid cross-linked with a polyfunctional agent is present in a concentration of between about 3.20% and about 3.40%; said lecithin-treated pigment is ultramarine blue, present in a concentration of between about 2.8% and about 3.2%; and said water is present in a concentration of between about 86% and about 89%.

10. A composition in accordance with claim 6 wherein said complex of triethanolamine and a polymer of acrylic acid cross-linked with a polyfunctional agent is present in a concentration of between about 3.175% and about 3.375%; said lecithin-treated pigment is iron oxide black, present in a concentration of between about 2.3% and about 2.7%; and said water is present in a concentration in the range of between about 85% and 88%.

* * * * *